(12) United States Patent
Maldonado et al.

(10) Patent No.: US 9,566,320 B2
(45) Date of Patent: Feb. 14, 2017

(54) MUCIN-ASSOCIATED SURFACE PROTEIN AS VACCINE AGAINST CHAGAS DISEASE

(71) Applicant: Board of Regents, The University of Texas System, Austin, TX (US)

(72) Inventors: Rosa A. Maldonado, El Paso, TX (US); Carylinda Serna, Silver Spring, MD (US); Igor C. Almeida, El Paso, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 14/494,812

(22) Filed: Sep. 24, 2014

(65) Prior Publication Data

US 2015/0086583 A1    Mar. 26, 2015

Related U.S. Application Data

(60) Provisional application No. 61/881,472, filed on Sep. 24, 2013.

(51) Int. Cl.

| | |
|---|---|
| A61K 39/00 | (2006.01) |
| A61K 39/002 | (2006.01) |
| A61K 39/385 | (2006.01) |
| A61K 39/38 | (2006.01) |
| A61K 38/00 | (2006.01) |
| C07K 2/00 | (2006.01) |
| C07K 4/00 | (2006.01) |
| C07K 5/00 | (2006.01) |
| C07K 7/00 | (2006.01) |
| C07K 14/00 | (2006.01) |
| C07K 16/00 | (2006.01) |
| C07K 17/00 | (2006.01) |
| A61K 39/005 | (2006.01) |
| C07K 14/14 | (2006.01) |
| C07K 14/445 | (2006.01) |

(52) U.S. Cl.
CPC ............ *A61K 39/005* (2013.01); *A61K 38/00* (2013.01); *A61K 39/00* (2013.01); *A61K 39/0011* (2013.01); *A61K 2039/545* (2013.01); *A61K 2039/55505* (2013.01); *A61K 2039/55516* (2013.01); *A61K 2039/575* (2013.01); *C07K 14/14* (2013.01); *C07K 14/445* (2013.01)

(58) Field of Classification Search
CPC .... A61K 39/00; A61K 39/0011; A61K 38/00; C07K 14/445; C07K 14/14
See application file for complete search history.

(56) References Cited

U.S. PATENT DOCUMENTS

| | | | |
|---|---|---|---|
| 4,298,596 | A | 11/1981 | Snary |
| 2010/0297186 | A1 | 11/2010 | de Baeremaecker Barros |
| 2011/0166063 | A1 | 7/2011 | Bossard et al. |
| 2011/0280901 | A1 | 11/2011 | Garg |
| 2012/0258126 | A1 | 10/2012 | Scholler et al. |

OTHER PUBLICATIONS

Mayo Clinic, http://www.mayoclinic.org/diseases-conditions/chagas-disease/basics/prevention/con-20030854, pp. 1-6, accessed on Mar. 30, 2016.*
Stills, ILAR Journal, 2005; 46(3): 281-293.*
Harris et al., Micron, 1999; 30: 597-623.*
Abbas, A. K. et al., "Functional diversity of helper T lymphocytes," Nature (1996) 383:787-793.
Abrahamsohn, I. A. et al. "*Trypanosoma cruzi*: IL-10, TNF, IFN-γ, and IL-12 Regulate Innate and Acquired Immunity to Infection," Experimental Parasitology (1996) 84:231-144.
Abrahamsohn, I. S. et al., "Effects of Interleukin-4 Deprivation and Treatment on Resistance to *Trypanosoma cruz*," Infection and Immunity (2000) 68(4):1975-1979.
Acosta-Serrano, A. et al., "Comparison and Evolution of the Surface Architecture of Trypanosomatid Parasites," Trypanosomes—After the Genome (2007), D. Barry, J. Mottram, R. McCulloch, and A. Acosta-Serrano (Eds.), Horizon Scientific Press, Norwich, UK, pp. 315-333.
Aliberti, J. C. S. et al., "Interleukin-12 Mediates Resistance to *Trypanosoma cruzi* in Mice and Is Produced by Murine Macrophages in Response to Live Trypomastigotes," Infection and Immunity (1996) 64(6):1961-1967.
Almeida, I. C. et al., "Complement-Mediated Lysis of *Trypanosoma cruzi* Trypomastigotes by Human Anti-α-Galactosyl Antibodies," The Journal of Immunology (1991) 146(7):2394-2400.
Almeida, I. C. et al., "Glycoconjugates of *Trypanosoma cruzi*: A 74 kD Antigen of trypomastigotes Specifically Reacts with Lytic Anti-α-Galactosyl Antibodies from Patients with Chronic Chagas Disease," Journal of Clinical Laboratory Analysis (1993) y:307-316.
Almeida, I. C. et al., "Lytic anti-α-galactosyl antibodies from patients with chronic Chagas' disease recognize novel *O*-linked oligosaccharides on mucin-like glycosyl-phosphatidylinositol-anchored glycoproteins of *Trypanosoma cruzi*," Biochem. J. (1994) 304:793-802.

(Continued)

Primary Examiner — Gary Nickol
Assistant Examiner — Lakia Tongue
(74) Attorney, Agent, or Firm — Norton Rose Fulbright US LLP

(57) ABSTRACT

Use of synthetic peptides derived from *Trypanosoma cruzi* antigens and their use in vaccination against trypomastigote infection and Chagas disease. *T. cruzi* uses several surface proteins to invade the host. In their role of protection, the surface protients ensure the targeting and invasion of specific cells or tissues. A conserved region in the family of mucin-associated surface proteins (MASP) was used to analyze the expression of MASP at different points of invasion and proved to be important for host cell invasion, thus suggesting MASP as a candidate for vaccine development. A synthetic peptide, MASPsyn, was studied and showed efficacy in stimulating antibody and cytokine production necessary for resistance against the parasite.

3 Claims, 4 Drawing Sheets

(56) References Cited

OTHER PUBLICATIONS

Almeida, I. C. et al., "A highly sensitive and specific chemiluminescent enzyme-linked immunosorbent assay for diagnosis of active *Trypanosoma cruzi* infenction," Transfusion (1997) 37:850-857.
Alsford, S. et al., "Genetic dissection of drug resistance in trypanosomes," Parasitology (2013) 140:1478-1491.
Andrews, N. W. et al., "Adhesion and Interiorization of *Trypanosoma cruzi* in Mammalian Cells," J. Protozool. (1982) 29(2):264-269.
Bartholomeu, D. C. et al., "Genomic organization and expression profile of the mucin-associated surface protein (*masp*) family of the human pathogen *Trypanosoma cruzi*," Nucleic Acids Research (2009) 37(10):3407-3417.
Bayer-Santos, E. et al., "Proteomic Analysis of *Trypanosoma cruzi* Secretome: Characterization of Two Populations of Extracellular Vesicles and Soluble Proteins," Journal of Proteome Research (2013) 12:883-897.
Boari, J. T. et al., "IL-17RA Signaling Reduces Inflammation and Mortality during *Trypanosoma cruzi* Infection by Recruiting Suppressive IL-10-Producing Neutrophils," PLoS Pathog. (2012) 8(4):e1002658, 17 pages.
Boscardin, S. B. et al., "Chagas' disease: an update on immune mechanisms and therapeutic strategies," J. Cell. Mol. Med. (2010) 14(6B):1373-1384.
Brodskyn, C. I. et al., "IgG subclasses responsible for immune clearance in mice infected with *Tryaponosoma cruzi*," Immunol. Cell Biol. (1989) 67:343-348.
Bryan, M. A. et al., "Specific Humoral Immunity versus Polyclonal B Cell Activation in *Trypanosoma cruzi* Infection of Susceptible and Resistant Mice," PLoS Negl. Trop. Dis (2010) 4(7):e733, 16 pages.
Carod-Artal, F. J. et al., "Chagas disease and stroke," Lancent Neurol (2010) 9:533-542.
Cordeiro, F. D. et al., "Anti-*Trypanosoma cruzi* Immunoglobulin G1 can be a Useful Tool for Diagnosis and Prognosis of Human Chagas' Disease," Clinical and Diagnostic Laboratory Immunology (2001) 8(1):112-118.
Cummings, K. L. et al., "Rapid quantitation of *Trypanosoma cruzi* in host tissue by real-time PCR," Molecular & Biochemical Parasitology (2003) 129:53-59.
Cunha-Neto, E. et al., "Myocardial gene and protein expression profiles after autoimmune injury in Chagas' disease cardiomyopathy," Autoimmunity Reviews (2011) 10:163-165.
De Araújo, F. F. et al., "Regulator T Cells Phenotype in Different Clinical Forms of Chagas' Disease," PLoS Negl. Trop. Dis. (2011) 5(5):e992, 8 pages.
De Pablos, L. M. et al., "Differential Expression and Characterization of a Member of the Mucin-Associate Surface Protein Family Secreted by *Trypanosoma cruzi*," Infection and Immunity (2011) 79(10):3993-4001.
De Pablos, L. M. et al., "Multigene Families in *Trypanosoma cruzi* and Their Role in Infectivity," Infection and Immunity (2012) 80(7):2258-2264.
Dos Santos, S. L. et al., "The MASP Family of *Trypanosoma cruzi*: Changes in Gene Expression and Antigenic Profile during the Acute Phase of Experimental Infection," PLoS Negl. Trop. Dis. (2012) 6(8):e1779, 14 pages.
El-Sayed, N. M. et al., "The Genome Sequence of *Trypanosoma cruzi*, Etiologic Agent of Chagas Disease," Science (2005) 309:409-415.
Galvão Da Silva, A. P. et al., "Resistant mice lacking interleukin-12 become susceptible to *Trypanosoma cruzi* infection but fail to mount a T helper type 2 response," Immunology (2003) 108:230-237.
Gascon, J. et al. "Chagas disease in Spain, the United States and other non-endemic countries," Acta Tropica (2010) 115:22-27.
Grauert, M. R. et al., "*Trypanosoma cruzi* infection enhances polyreactive antibody response in an acute case of human Chagas' disease," Clin. Exp. Immunol. (1993) 93:85-92.
Guedes, P. MdM. et al., "IL-17 Produced during *Trypanosoma cruzi* Infection Plays a Central Role in Regulating Parasite-Induced Myocarditis," PLoS Negl. Trop. Dis. (2010) 4(2):e604, 11 pages.
Hoft, D. F. et al., "Involvement of $CD4^+$ Th1 Cells in Systemic Immunity Protective against Primary and Secondary Challenges with *Trypanosoma cruzi*," Infection and Immunity (2000) 68(1):197-204.
Hölscher, C. et al., "Tumor Necrosis Factor Alpha-Mediated Toxic Shock in *Trypanosoma cruzi*-Infected Interleukin 10-Deficient Mice," Infection and Immunity (2000) 68(7):4075-4083.
Hunter, C. A. et al., "IL-10 is Required to Prevent Immune Hyperactivity During infection with *Trypanosoma cruzi*," The Journal of Immunology (1997) 158:3311-3316.
Jäger, A. et al., "Th1, Th17, and Th9 Effector Cells Induce Experimental Autoimmune Encephalomyelitis with Different Pathological Phenotypes," The Journal of Immunology (2009) 183:7169-7177.
Kierszenbaum, F., "Protection of Congenitally Athymic Mice Against *Trypanosoma cruzi* Infection by Passive Antibody Transfer," J. Parasitol. (1980) 66(4):673-675.
Korn, T. et al., "IL-17 and Th17 Cells," Annu. Rev. Immunol. (2009) 27:485-517.
Krettli, A. U. et al., "Protective Effects of Specific Antibodies in Trypanosoma Cruzi Infections," The Journal of Immunology (1976) 116(3):755-760.
Krettli, A. U. et al., "Membrane-bound antibodies to bloodstream *Trypanosoma cruzi* in mice: strain differences in susceptibility to complement-mediated lysis," Clin. Exp. Immunol. (1979) 37:416-423.
Krettli, A. U., "The utility of anti-trypomastigote lytic antibodies for determining cure of *Trypanosoma cruzi* infections in treated patients: an overview and perspectives," Mem Inst Oswaldo Cruz, Rio de Janeiro (2009) 104 (Suppl. I):142-151.
Kumar, S. et al., "The relative contribution of antibody production and $CD8^+$ T cell function to immune control of *Trypanosoma cruzi*," Parasite Immunology (1998) 20:207-216.
Kumar, S. et al., "Antigen-Specific Th1 But Not Th2 Cells Provide Protection from Lethal *Trypanosoma cruzi* Infection in Mice," The Journal of Immunology (2001) 166:4596-4603.
Lee, B. Y. et al., "Modeling the economic value of a Chagas' disease therapeutic vaccine," Human Vaccines & Immunotherapeutics (2012) 8(9):1293-1301.
Lee, B. Y. et al., "Global economic burden of Chagas disease: a computational simulation model," Lancet Infect. Dis (2013) 13(4):342-348.
Lima, E. C. S. et al., "Evidence for a Protective Role of Tumor Necrosis Factor in the Acute Phase of *Trypanosoma cruzi* Infection in Mice," Infection and Immunity (1997) 65(2):457-465.
Magalhães, L. M. D. et al., "High Interleukin 17 Expression Is Correlated with Better Cardiac Function in Human Chagas Disease," The Journal of Infectious Diseases (2013) 207:661-665.
Michailowsky, V. et al., "Pivotal Role of Interleukin-12 and Interferon-$\gamma$ Axis in Controlling Tissue Parasitism and Inflammation in the Heart and Central Nervous System during *Trypanosoma cruzi* Infection," American Journal of Pathology (2001) 159(5):1723-1733.
Michailowsky, V. et al., "Humoral and Cellular Immune Responses to *Tryapnosoma cruzi*-Derived Paraflagellar Rod Proteins in Patients with Chagas' Disease," Infection and Immunity (2003) 71(6):3165-3171.
Miyazaki, Y. et al., "IL-17 Is Necessary for Host Protection against Acute-Phase *Trypanosoma cruzi* Infection," The Journal of Immunology (2010) 185:1150-1157.
Morrot, A. et al., "Dynamics of Lymphocyte Populations during *Trypanosoma cruzi* infection: From Thymocyte Depletion to Differential Cell Expansion/Contraction in Peripheral Lymphoid Organs," Journal of Tropical Medicine (2012) 2012(747185): 7 pages.
Murta, S. M. F. et al., "Differential gene expression in *Trypanosom cruzi* populations susceptible and resistant to benznidazole," Acta Tropica (2008) 107:59-65.
Nakayasu, E. S. et al., "Improved Proteomic Approach for the Discovery of Potential Vaccine Targets in *Trypanosoma cruzi*," Journal of Proteome Research (2012) 11:237-246.

(56) References Cited

OTHER PUBLICATIONS

Nielsen, M. et al., "Prediction of MHC class II binding affinity using SMM-align, a novel stabilization matrix alignment method," BMC Bioinformatics (2007) 8:238, 12 pages.
Nielsen, M. et al, "NN-align. An artificial neural network-based alignment algorithm for MHC class II peptide binding prediction," BMC Bioinformatics (2009) 10:296, 10 pages.
Okabe, K. et al., "Cell-Mediated Cytotoxicity to *Trypanosoma cruzi*," Clinical Immunology and Immunopathology (1980) 16:344-353.
Pereira-Chioccola, V. L. et al., "Mucin-like molecules form a negatively charged coat that protects *Trypanosoma cruzi* trypomastigotes from killing by human anti-α-galactosyl antibodies," Journal of Cell Science (1000) 113:1299-1307.
Pérez, A. R. et al., "Extrathymic CD4$^+$CD8$^+$ lymphocytes in Chagas disease: possible relationship with an immunoendocrine imbalance," Ann. N.Y. Acad. Sci. (2012) 1262:27-36.
Pinazo M.-J. et al., "Tolerance of Benznidazole in Treatment of Chagas' Disease in Adults," Antimicrobial Agents and Chemotherapy (2010) 54(11):4896-4899.
Primavera, K. S. C. et al., "Chagas' Disease: IgA, IgM and IgG Antibodies to T. cruzi Amastigote, Trypomastigote and Epimastigote Antigens in Acute and in Different Chronic Forms of the Disease," Rev. Inst. Med. Trop. São Paulo (1990) 32(3):172-180.
Quijano-Hernandez, I. et al., "Advances and challenges toward a vaccine against Chagas disease," Human Vaccines (2011) 7(11):1184-1191.
Rassi, Jr, A. et al., "America Trypanosomiasis (Chagas Disease)," Infect. Dis. Clin. N. Am. (2012) 26:275-291.
Rottenberg, M. E. et al., "Differential Susceptibilities of Mice Genornically Deleted of CD4 and CD8 to Infections with *Trypanosoma cruzi* or *Trypanosoma brucei*," Infection and Immunity (1993) 61(12):5129-5133.
Singh, H. et al., "ProPred: prediction of HLA-DR binding sites," Bioinformatics (2001) 17(12):1236-1237.
Singh, H. et al., "ProPred1: prediction of promiscuous MHC Class-I binding sites," Bioinformatics (2003) 19(8):1009-1014.
Sturniolo, T. et al., "Generation of tissue-specific and promiscuous HLA ligand databases using DNA microarrays and virtual HLA ciass II matrices," Nature Biotechnology (1999) 17:555-561.

Takehara, H. A. et al., "A comparative study of anti-*Trypanosoma cruzi* serum obtained in acute and chronic phase of infection in mice," Immunology Letters (1989/1990) 23:81-86.
Tarleton, R. L. et al., "Susceptibility of $\beta_2$-microglobulin-deficient mice to *Trypanosoma cruzi* infection," Nature (1992) 356:338-340.
Tosello Boari, J. et al., "1L-17RA Signaling Reduces Inflammation and Mortality during *Trypanosoma cruzi* Infection by Recruiting Suppressive IL-10-Producing Neutrophils," PLoS Pathog (2012) 8(4):e1002658, 17 pages.
Travassos, L. R. et al., "Carbohydrate immunity in American trypanosomiasis," Sprinter Semin Immunopathol (1993) 15:183-204.
Vasconcelos, J. R. et al., "Protective Immunity Against *Trypanosoma cruzi* Infection in a Highly Susceptible Mouse Strain After Vaccination with Genes Encoding the Amastigote Surface Protein-2 and *Trans*-Sialidase," Human Gene Therapy (2004) 15:878-886.
Vázquez-Chagoyán, J. C. et al., "Vaccine Development Against *Trypanosoma cruzi* and Chagas Disease," Advances in Parasitology (2011) L. M. Weiss, H. B. Tanowitz, and L. V. Kirchhoff (eds.) Burlington: Academic Press, vol. 75, pp. 121-145.
Wang, P. et al., "A Systematic Assessment of MHC Class II Peptide Binding Predictions and Evaluation of a Consensus Approach," PLoS Comput Biol (2008) 4(4):e1000048, 11 pages.
Wurster, A. L. et al., "Interleukin-4-mediated Protection of Primary B Cells from Apoptosis through Stat6-dependent Up-regulation of Bcl-xL," The Journal of Biological Chemistry, (2002) 277(30):27169-27175.
PCT International Search Report for PCT/US2014/057124 dated Mar. 13, 2015.
Brener, Z, "Therapeutic Activity and Criterion of Cure on Mice Experimentally Infected with Trypanosoma Cruzi," Rev. Inst. Med. trop. Sao Paulo (1962) 4(6):389-396.
Junqueira, C. et al., "The endless race between Trypanosoma cruzi and host immunity: lessons for and beyond Chagas disease," Expert Reviews in Molecular Medicine (2010) 12:e29, 23 pages.
Lima-Martins, M. V. C. et al., "Antibody-dependent cell cytotoxicity against Trypanosoma cruzi is only mediated by protective antibodies," Parasite Immunology (1985) 7:367-376.
Lages Silva, E. et al., "Effective of protective and non-protective antibodies in the phagocytosis rate of Trypanosoma cruzi blood forms by mouse peritoneal macrophages," Parasite Immunology (1987) 9:21-30.

\* cited by examiner

| Allele | Predicted Binding Site | Score |
| --- | --- | --- |
| HLA-A1 | DAENPGGEVFNDNKKGLSRV | 12.2 |
| HLA-A24 | DAENPGGEVFNDNKKGLSRV | 48.59 |
| HLA-B*2702 | DAENPGGEVFNDNKKGLSRV | 10.66 |
| HLA-B*2705 | DAENPGGEVFNDNKKGLSRV | 32.99 |
| HLA-B*3701 | DAENPGGEVFNDNKKGLSRV | 8.66 |
| HLA-B*3801 | DAENPGGEVFNDNKKGLSRV | 17.46 |
| HLA-B*3902 | DAENPGGEVFNDNKKGLSRV | 12.65 |
| HLA-B40 | DAENPGGEVFNDNKKGLSRV | 32.71 |
| HLA-B*4403 | DAENPGGEVFNDNKKGLSRV | 43.35 |
| HLA-B*5101 | DAENPGGEVFNDNKKGLSRV | 52.16 |
| HLA-B*5102 | DAENPGGEVFNDNKKGLSRV | 34.34 |
| HLA-B*5103 | DAENPGGEVFNDNKKGLSRV | 63.38 |
| HLA-B*5201 | DAENPGGEVFNDNKKGLSRV | 22.95 |
| HLA-B*5401 | DAENPGGEVFNDNKKGLSRV | 65.89 |
| HLA-B*51 | DAENPGGEVFNDNKKGLSRV | 71.01 |

FIG. 4

SEQUENCE LISTING

<160> NUMBER OF SEQ ID NOS: 5

<210> SEQ ID NO 1
<211> LENGTH: 20

```
<212> TYPE: PRT
<213> ORGANISM: Artificial sequence
<220> FEATURE:
<223> OTHER INFORMATION: Based on Trypanosoma cruzi

<400> SEQUENCE: 1

Asp Ala Glu Asn Pro Gly Gly Glu Val Phe Asn Asp Asn Lys Lys Gly
1               5                   10                  15

Leu Ser Arg Val
            20

<210> SEQ ID NO 2
<211> LENGTH: 20
<212> TYPE: DNA
<213> ORGANISM: Artificial sequence
<220> FEATURE:
<223> OTHER INFORMATION: Primer

<400> SEQUENCE: 2
gctcttgccc acamgggtgc                                           20

<210> SEQ ID NO 3
<211> LENGTH: 21
<212> TYPE: DNA
<213> ORGANISM: Artificial sequence
<220> FEATURE:
<223> OTHER INFORMATION: Primer

<400> SEQUENCE: 3
ccaagcagcg gatagttcag g                                         21

<210> SEQ ID NO 4
<211> LENGTH: 25
<212> TYPE: DNA
<213> ORGANISM: Artificial sequence
<220> FEATURE:
<223> OTHER INFORMATION: Primer

<400> SEQUENCE: 4
tccctctcat cagttctatg gccca                                     25

<210> SEQ ID NO 5
<211> LENGTH: 27
<212> TYPE: DNA
<213> ORGANISM: Artificial sequence
<220> FEATURE:
<223> OTHER INFORMATION: Primer

<400> SEQUENCE: 5
cagcaagcat ctatgcactt agacccc                                   27
```

MUCIN-ASSOCIATED SURFACE PROTEIN AS VACCINE AGAINST CHAGAS DISEASE

CROSS-REFERENCE TO RELATED APPLICATIONS

The present application is related to and claims priority to U.S. provisional patent application Ser. No. 61/881,472, filed Sep. 24, 2013, the entirety of which is incorporated by reference herein.

GOVERNMENT RIGHTS STATEMENT

This invention was made with government support under 2S06GM00812-37 awarded by the National Institutes of Health. The government has certain rights in the invention.

TECHNICAL FIELD

The present invention relates to the field of human health and in particular to vaccination approaches for control of *Trypanosoma cruzi* infection and Chagas disease.

BACKGROUND OF THE INVENTION

*Trypanosoma cruzi* (*T. cruzi*) is a flagellate protozoan that causes Chagas disease. Chagas disease affects millions of people worldwide and has become a larger concern in the United States with growing numbers of immigrant population. The human infection begins with the metacyclic trypomastigote form, present in the vector's (triatomine) feces. The infection is introduced into the blood stream through the bite wound or mucosal tissues. After infection, the metacyclic form of this parasite transforms into the proliferative amastigote, which then transforms into trypomastigotes in the host cells. The trypomastigotes are released into the bloodstream and go onto infect other cells and tissues. The parasite can also be transmitted through other routes such as blood transfusion, organ transplant, and congenital transmission. Currently, benznidazole and nifurtimox are the only available drugs for treating Chagas disease, which are extremely toxic, less effective in the chronic stage (especially the late chronic stage), and a growing number of resistant strains are arising. While vaccination has been demonstrated to be a cost-effective approach to illness and death caused by infectious diseases, there is not yet an effective vaccine for Chagas disease.

BRIEF DESCRIPTION OF THE FIGURES

The accompanying figures, in which like reference numerals refer to identical or functionally-similar elements throughout the separate views and which are incorporated in and form a part of the specification, further illustrate the embodiments and, together with the detailed description, serve to explain the embodiments disclosed herein.

FIG. 4 contains common alleles within at-risk populations and predicted binding sites (underlined portions) for MASPsyn, which has the amino acid sequence of SEQ ID NO:1.

DETAILED DESCRIPTION

Figure 1:
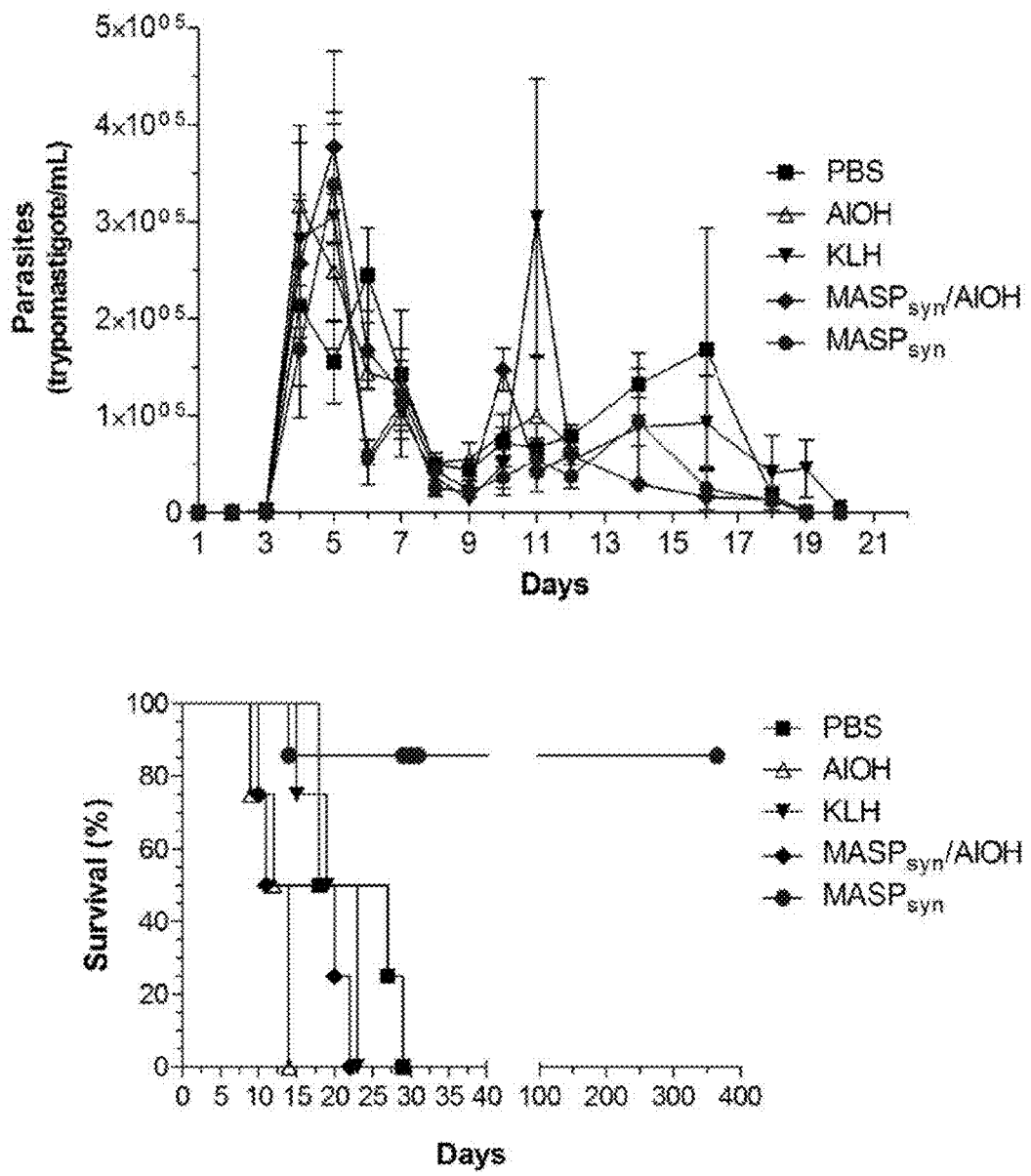
FIG. 1 illustrates resulting parasitemia and survival for each of he control and experimental groups.

The embodiments will now be described more fully hereinafter with reference to the accompanying drawings, in which illustrative embodiments of the invention are shown. The embodiments disclosed herein can be embodied in many different forms and should not be construed as limited to the embodiments set forth herein; rather, these embodiments are provided so that this disclosure will be thorough and complete, and will fully convey the scope of the invention to those skilled in the art. Unnecessary detail of known functions and operations may be omitted from the current description so as not to obscure the present invention. Like numbers refer to like elements throughout. As used herein, the term "and/or" includes any and all combinations of one or more of the associated listed items.

The terminology used herein is for the purpose of describing particular embodiments only and is not intended to be limiting of the invention. As used herein, the singular forms "a", "an", and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The term "antigen" as used herein is defined as a compound, composition, or substance that can stimulate the production of antibodies or a T-cell response in an animal or human, including compositions that are injected or absorbed. An antigen reacts with the products of specific humoral or cellular immunity, including those induced by heterologous immunogens. The term "antigen" includes all related antigenic epitopes. "Epitope" refers to a site on an antigen that is recognized by the immune system, specifically by antibodies, B cells, or T cells.

The term "antibody" as used herein includes immunoglobulin molecules and immunologically active portions of immunoglobulin molecules utilized by the immune system to identify and neutralize foreign objects within the body, such as bacteria and viruses. Antibodies are typically composed of basic structural units—each with two large heavy chains and two small light chains. There are several different types of antibody heavy chains and several different kinds of antibodies, which are grouped into different isotypes based on which heavy chain they possess. Five different antibody isotypes are known in mammals, which perform different roles, and help direct the appropriate immune response for each different type of foreign object they encounter. It has been shown that the antigen-binding function of an antibody can also be performed by fragments of a naturally occurring antibody. Thus, these antigen-binding fragments are also intended to be designated by the term "antibody."

The term "cytokines" as used herein encompasses a group of small proteins that are important to cell signaling. Cytokines are released by cells and affect the behavior of other cells, and sometimes the releasing cell itself. They act through receptors and are especially important in the immune system as cytokines modulate the balance between humoral and cell-based immune responses, and they regulate the maturation, growth, and responsiveness of particular cell populations. Non-limiting examples of cytokines include chemokines, interferons, interleukins, lymphokines, and tumour necrosis factor. Cytokines are produced by a broad range of cells, including immune cells like macrophages, B lymphocytes, T lymphocytes, and mast cells. A given cytokine may be produced by more than one type of cell.

*T. cruzi* is encompassed by a thick layer of glycosylphosphatidylinositol (GPI)-anchored proteins that are encoded by multigene families like mucins (TcMUC), mucin associated surface proteins (MASP), trans-sialidase/gp85, and gp63 glycoproteins. MASP was first described upon the completion of the *T. cruzi* genome and it is now known to be the second largest gene family with 1,377 genes, about 6% of the *T. cruzi* genome. Like other GPI-anchored proteins, they have a highly conserved N- and C-terminal regions and possess N-O-glycosylated regions. Furthermore, since this family does not have any genes orthologous to other sequenced kinetoplastid, it makes it very specific to *T. cruzi*.

*T. cruzi* uses several of these surface proteins to invade the host. In their role of protection, they ensure the targeting and invasion of specific cells or tissues. A conserved region in the family of MASP was used to analyze the expression of MASP at different points of invasion. It was found that there was an increase of expression in trypomastigote and amastigote forms of PAN4 and CL-Brener strains. This supported the already establish notion that MASP is upregulated in the infectious stages. Proteins found on the surface of the parasite such as prolyl oligopeptidase (POP Tc80) have also been shown to be secreted in the culture medium of infectious forms of the parasite. Also, MASP52, obviously part of the MASP family, was shown to play a role in the process of host invasion, as well as being secreted by metacyclic typomastigote. In other work, antibodies against a conserved motif of MASPs reacted to the supernatant of parasites, leading to the belief that MASP family members are shed into the culture medium. Hence, MASP is important for host cell invasion. MASP is up regulated in resistant strains of *T. cruzi* compared to those susceptible to benznidazole, therefore, suggesting that MASP could be a good target for vaccine development.

The ideal vaccine against the complex intracellular and extracellular *T. cruzi* is one that can elicit both a humoral and cellular immune response. The ability of a synthetic peptide (MASPsyn) having an amino acid sequence represented by DAENPGGEVFNDNKKGLSRV (SEQ ID No. 1) (also referred to as MASPpep), conjugated with keyhole limpet hernocyanin (KLH) to provide protection against *T cruzi* was studied. Though KLH was used in the study, other pharmaceutically acceptable carriers may be combined with the MASPsyn in order to enhance immunogenicity. The study also attempted to stimulate the immune response with a known human adjuvant aluminum hydroxide (AlOH) because of its known role in stimulating CD4+ T cells. AlOH was shown to stimulate a Th1-type immune response and help regulate the infection. Based on in silico analysis, MASPsyn has the characteristics to be able to stimulate the adequate immune response and thus help control parasite amount and/or increase survivability of the host. In order to address, experiments were conducted that showed that MASPsyn, without the aid of any additional adjuvants, was able to stimulate antibody and cytokine (e.g., IL-4, IL-10, IL-12, IL-17A, and IFN-γ) production that are crucial for resistance against the parasite, as well as increase survivability to immunized-infected mice.

In Vitro and in Vivo Trypomastigote Culture

*T. cruzi* Y strain trypomastigotes were kept in culture by alternating infecting BALB/c mice and monkey kidney epithelial cells. After five passages, BALB/c mice were infected with $1 \times 10^4$ trypomastigotes. After 3 days, bloodstream trypomastigotes were obtained and were used to infect LLC-MK2. Cells were kept at 37° C. in a humid atmosphere supplemented with 5% $CO_2$ in Dulbecco's modified Eagle's medium (DMEM) containing 10% inactivated fetal calf serum and 5% antibiotics (ampicillin/streptomycin).

Selection and Production of the Synthetic MASPsyn

Using adequate computational analyses (ABCpred prediction server for B cell epitope recognition, ProPred I, SYPEITHI, and HLA-BP for MHC I, and TEPITOPE and ProPred for MHC II recognition) a peptide from the protein that seemed to have a high score of epitope recognition in B-cell recognition was chosen, MHC I, and MHC II in humans and mice. The MASPsyn peptide was then synthesized utilizing convention techniques. The peptide was then conjugated to KLH.

Immunization

C3H/HeNsd female mice (6-8 weeks old) were separated in five groups (4 mice/group). The immunizations were performed via intraperitoneal (i.p.) injection. One control group was immunized with phosphate buffer saline (PBS, placebo). Two control groups for the adjuvants were given 0.9% aluminum hydroxide (AlOH) and KLH at 10 μg/mouse. Two experimental groups were administered 20 μg/mouse of MASPsyn alone and combined with 0.9% aluminum hydroxide, respectively. A total of 3 immunizations every 10-15 days were administered.

Evaluation of the Humoral Immune Response

Ten days after the last immunization blood was collected by tail bleeding and serum was separated from blood by centrifugation at 2,000 rpm for 10 min. The serum antibody titers were determined by an ELISA. Human Chagasic and normal serum were also tested for antibody titers against MASPsyn.

Immunoglobulin Isotyping

Immunoglobulin isotyping was examined using Mouse Immunoglobulin Isotyping ELISA Kit. The serum from the placebo and MASPsyn immunized groups was obtained as described above. The positive control was provided in the kit. The assay was performed following the manufacture guidelines; each sample was done in triplicate and read at an absorbance of 450 nm using a microplate reader.

Trypomastigote Lysis Assay

Pool of serum was collected from both non-infected placebo (complement system active) and MASPsyn immunized mice (inactivated complement system, 56° C. for 30 min). Trypomastigote suspensions (200 μL of 1×107 parasites/mL in DMEM) were incubated with 0.8 μL (1:250) of either serum at 37° C. for 1 hr. Then, propidium iodine (PI) was added (0.5 μg/mL) and cells were incubated for 5 min. at 24° C., followed by three washes with PBS. The pellet was re-suspended in 4% paraformaldehyde, incubated at 24° C. for 15 minutes, and then washed with PBS. Finally, the pellet was re-suspended in 300 μL PBS. The positive and negative controls (live and dead parasites, respectively) were prepared similarly. Briefly, the trypomastigote suspension (200 μL of 1×107 parasites/mL in DMEM) was washed three times with PBS and PI was added (0.5 μg/mL), then followed by three washes with PBS, the parasites were then fixed with 4% paraformaldehyde, followed by three PBS washes, and finally resuspended in 300 μL PBS. In the negative control, the trypomastigote suspension was treated with hydrogen peroxide (200 μM), then washed with PBS, the pellet was resuspended in PI (0.5 μg/mL), then followed by three washes with PBS, the parasites were then fixed with 4% paraformaldehyde, followed by three PBS washes, and finally resuspended in 300 μL. PBS. The samples were evaluated by flow cytometry. The experiment was performed in triplicate in three independent experiments. For each individual sample, approximately 10,000 events were acquired and analyzed using specialized software. The results were plotted as a percentage of dead parasites.

Challenge - Parasitemia and Survival

Ten days after last immunization mice were inoculated via intraperitoneal injection with $1\times10^5$ trypomastigote Y strain, the parasitemia and survival were monitored. The parasitema were evaluated every day for the first 12 days then every third day for a total of 21 days. FIG. 1 illustrates the resulting parasitemia and survival for each of the control and experimental groups.

Evaluation of Cytokines

Figure 2:
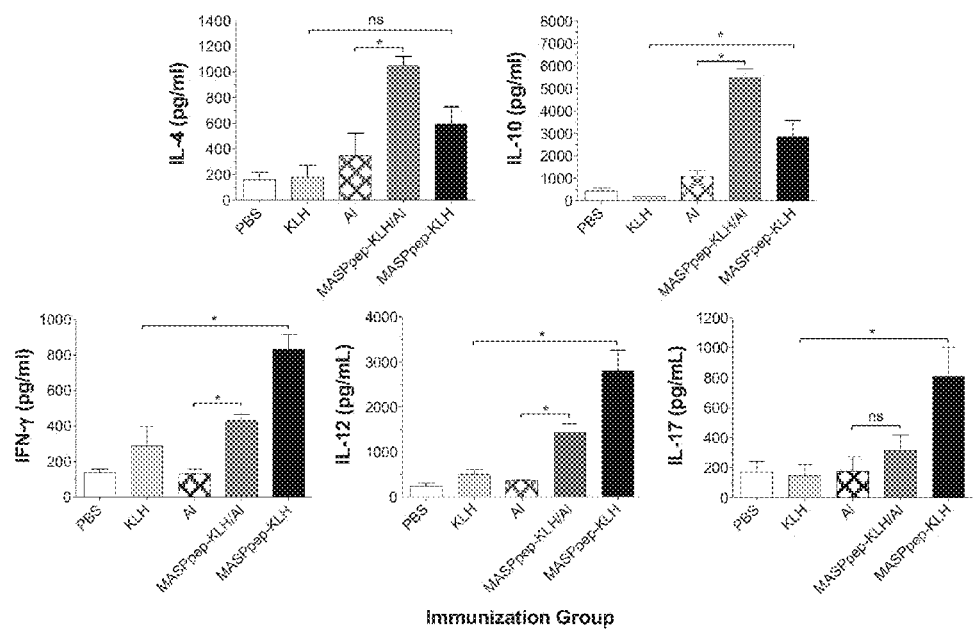
FIG. 2 illustrates cytokine profiles of immunized mice following parasite challenge.

Four weeks post-infection, the blood was collected by tail-bleeding and a pool of serum from each experimental group was obtained as described above. Cytokines were measured using Mouse Inflammatory Cytokines Multi-analyte ELISArray Kit. FIG. 2 illustrates cytokine profiles of immunized mice following parasite challenge. Anti-inflammatory (IL-4 and IL-10) and proinflammatory (IFN-γ, IL-12, and IL-17) cytokines were assayed in triplicate by ELISA four weeks after the last immunization and approximately two weeks after the challenge. Each bar represents the mean value±SEM (n=4 animals per group) for each treatment.

DNA Preparation

In the terminal stage of the disease, mice were euthanized and the heart, liver, and spleen tissues were collected. This procedure was performed at different end points upon the protection offered by the immunization. DNA was extracted and quantified by spectrophotometer.

Real-time PCR

Each PCR reaction contained 50 ng genomic DNA, 0.5 μM of T. cruzi 195-bp repeat DNA-specific primers TCZ-F 5'GCTCTTGCCCACAMGGGTGC-3' (SEQ ID NO. 2) where M=A or C and TCZ-R 5'-CCAAGCAGCGGATAGT-TCAGG-3' (SEQ ID NO. 3) primers. In addition, 12.5 μL of IQ SYBR Green Supermix and RT-PCR-grade water was added to a final volume of 25 μL. Independently, reactions containing 50 ng genomic DNA, 0.5 μM of murine-specific tumor necrosis factor-α (TNFα) primers TNF-5241 5-TC-CCTCTCATCA-GTTCTATGGCCCA-3' (SEQ ID NO. 4) and TNF 5411 5'-CAGCAAGCATCTATGCACTTAGAC-CCC-3' (SEQ ID NO. 5), 12.5 μL. of IQ SYBR Green Supermix and RT-PCR-grade water were added to a final volume of 25 μL. Negative controls with no DNA added were done. All reactions were performed in triplicate. The reactions were placed onto a 96-well plate (Bio-Rad, Hercules, Calif.), centrifuged for 2 min at 2000 rpm, and placed in the Eppendorf Mastercycler ep Realplex (Eppendorf, Hauppauge, N.Y.). The reactions were exposed to four phases: denaturation, amplification, melting, and cooling. In the denaturation phase, the plate is heated to 95° C. for 2 min, the amplification was done during 35 cycles for T. cruzi primers (45 cycles for TNFα primers) at three steps: 95° C. for 15 s, then 65° C. for 10 s, 72° C. for a 5 a hold, and then 79° C. for 20 seconds, at which the fluorescence intensity is acquired. The melt phase then begins with 95° C. for 15 seconds, then 60° C. for 15 seconds, and finally 95° C. for 15 second hold. Also, the amplification products for each sample were subjected to ethidium bromide, ran through an electrophoresis 1% agarose gel, and finally viewed under UV light. Briefly, to 150 mg of normal tissue was added $3\times10^6$ T. cruzi trypomastigotes and then the DNA was extracted and quantified. The standard curve obtained was used to determine the parasite load of infected tissues.

In Vivo Depletion of Immune Cell Subsets

Figure 3:
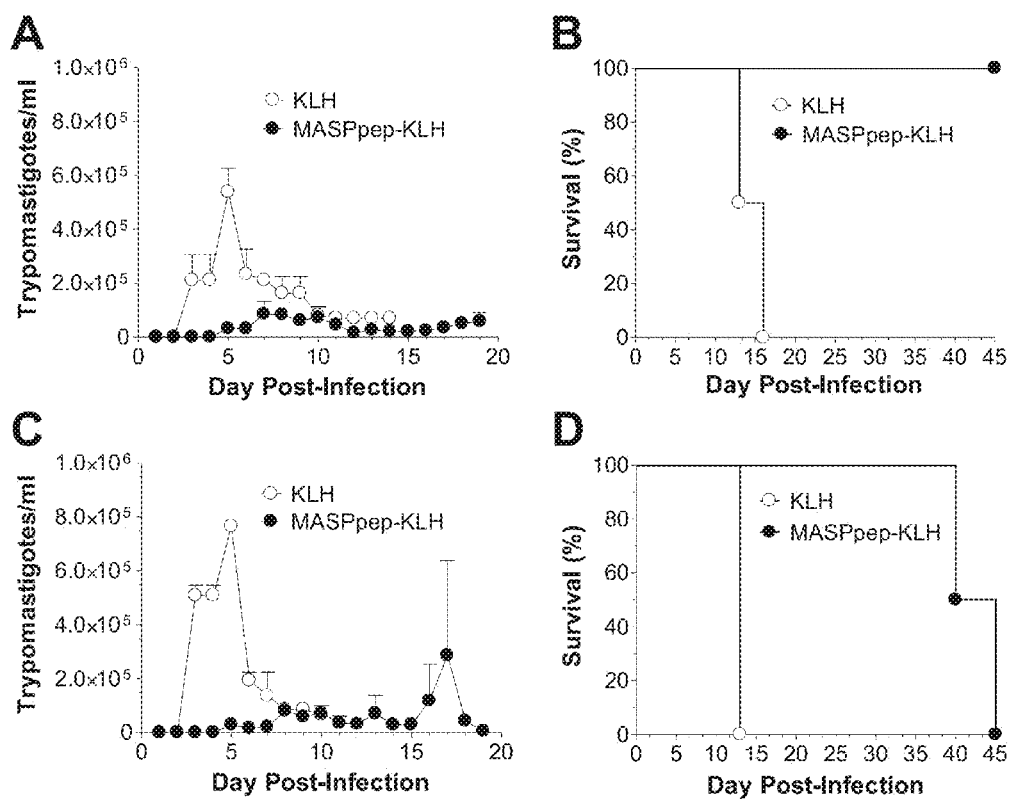
FIG. 3 illustrates the effect of in vivo depletion of CD4+ or CD8+ T cells in mice immunized with KLH or MASPsyn-KLH and Kaplan-Meier curves for survival and parasitemia of mice immunized with MASPsyn-KLH or KLH, and then treated with anti-CD4 or anti-CD8 mAbs.

One week after the last immunization, mice received i.p. injections of 500 μg anti-CD4 or 1000 μg of anti-CD8 mAbs, Unspecific IgG was given to the control groups. Depletion was analyzed by flow and the data were acquired using a flow cytometer. For each individual sample, approximately 10,000 events were acquired and analyzed. Mice were then challenged with $1\times10^5$ trypomastigotes 48 hours after last dose of anti-CD4/CD8. Parasitemia and survival were followed as previously described. FIG. 3. illustrates the effect of in viva depletion of CD4+ or CD8+ T cells in mice immunized with KLH or MASPsyn-KLH and Kaplan-Meier curves for survival and parasitemia of mice immunized with MASPsyn-KLH or KLH, and then treated with anti-CD4 (A and B) or anti-CD8 mAbs (C and D). N=2 animals per group.

It should be noted that based on immunoinformatic analysis through the Allele Frequency Net Database available on the world wide web at allelefrequencies.neti), the combination of putative MHC-I and MHC-II epitopes on MASPsyn, may be able to elicit immune responses in approximately 22 to 90% of the population in endemic countries such as Bolivia, Brazil, Peru, and Venezuela. FIG. 4 contains common alleles within these populations and predicted binding sites for MASPsyn. This suggests that further experimental studies should be conducted to validate MASPsyn as potential candidate for a vaccine against Chagas disease in humans. It should also be noted that while MASPsyn has been studied as a monocomponent vaccine, there is evidence to suggest that it can be effective if included in a multiple antigen vaccine as well.

It will be appreciated that variations of the above-disclosed and other features and functions, or alternatives thereof, may be desirably combined into many other different systems or applications. Also, that various presently unforeseen or unanticipated alternatives, modifications, variations or improvements therein may be subsequently made by those skilled in the art which are also intended to be encompassed by the following claims.

What is claimed is:

1. A pharmaceutical composition comprising: a peptide comprising an antigen consisting of the amino acid sequence of DAENPGGEVFNDNKKGLSRV (SEQ ID NO: 1); and an immune-effective amount of (i) an adjuvant or (ii) a conjugate of said antigen.

2. The pharmaceutical composition of claim 1 wherein the adjuvant is aluminum hydroxide.

3. The pharmaceutical composition of claim 1 wherein the peptide is conjugated to keyhole limpet hemocyanin.

* * * * *

UNITED STATES PATENT AND TRADEMARK OFFICE
CERTIFICATE OF CORRECTION

PATENT NO. : 9,566,320 B2  
APPLICATION NO. : 14/494812  
DATED : February 14, 2017  
INVENTOR(S) : Rosa A. Maldonado et al.

It is certified that error appears in the above-identified patent and that said Letters Patent is hereby corrected as shown below:

In the Specification

Column 1, Line 15: please delete "2S06GM00812-37" and substitute therefor --2S06GM008012-37--

Signed and Sealed this  
Fourth Day of July, 2017

Joseph Matal  
*Performing the Functions and Duties of the*  
*Under Secretary of Commerce for Intellectual Property and*  
*Director of the United States Patent and Trademark Office*